United States Patent
Liu

(10) Patent No.: US 10,279,063 B2
(45) Date of Patent: May 7, 2019

(54) STERILIZATION BOX

(71) Applicant: IPM KOREA Co,. Ltd, Seoul (KR)

(72) Inventor: Shunqi Liu, Seoul (KR)

(73) Assignee: IPM KOREA Co,. Ltd, Seoul (KR)

( * ) Notice: Subject to any disclaimer, the term of this patent is extended or adjusted under 35 U.S.C. 154(b) by 0 days.

(21) Appl. No.: 15/634,139

(22) Filed: Jun. 27, 2017

(65) Prior Publication Data
US 2018/0140732 A1  May 24, 2018

(30) Foreign Application Priority Data

Nov. 23, 2016 (CN) .......................... 2016 1 1059401

(51) Int. Cl.
*A61L 2/26* (2006.01)
*A61L 2/10* (2006.01)
*A46B 17/06* (2006.01)

(52) U.S. Cl.
CPC .............. *A61L 2/26* (2013.01); *A46B 17/065* (2013.01); *A61L 2/10* (2013.01); *A61L 2202/11* (2013.01); *A61L 2202/122* (2013.01); *A61L 2202/123* (2013.01); *A61L 2202/182* (2013.01); *A61L 2202/20* (2013.01)

(58) Field of Classification Search
CPC . A61L 2/00; A61L 2/0047; A61L 2/10; A61L 2/26
USPC ................ 250/492.1, 453.11, 454.11, 455.11
See application file for complete search history.

(56) References Cited

U.S. PATENT DOCUMENTS

| | | | | |
|---|---|---|---|---|
| 4,740,706 A | * | 4/1988 | Murdock, III | A61L 2/10 250/455.11 |
| 5,023,460 A | * | 6/1991 | Foster, Jr. | A61L 2/10 250/455.11 |
| 5,127,521 A | * | 7/1992 | Bourque | A61L 2/10 206/15.2 |
| 2004/0258559 A1 | * | 12/2004 | Paskal | A46B 17/06 422/26 |

* cited by examiner

Primary Examiner — Jason L McCormack
(74) Attorney, Agent, or Firm — Perkins Coie LLP

(57) ABSTRACT

The present application belongs to the technical field of household commodity and provides a sterilization box applicable to sterilize cosmetic tools, which comprises a base assembly, a housing assembly connected to the base assembly and cooperating with the base assembly to form a first cavity, and a supporting assembly connected in the first cavity and being able to connect with a plurality of cosmetic tools. The base assembly is provided therein with a second cavity. The sterilization box further comprises a circulation assembly configured to drive air circulations in the first cavity and in the second cavity and a sterilization assembly configured to sterilize the cosmetic tools. The circulation assembly includes a first ventilation assembly cooperating with the second cavity and a second ventilation assembly cooperating with the first cavity. A heating assembly cooperating with the first ventilation assembly is connected in the second cavity.

6 Claims, 5 Drawing Sheets

STERILIZATION BOX

CROSS REFERENCE TO RELATED APPLICATIONS

This application claims priority to CN 201611059401.X filed Nov. 23, 2016 and is hereby incorporated by reference.

TECHNICAL FIELD

The present application belongs to the technical field of household commodity, and particularly relates to a sterilization box.

BACKGROUND

In the present household and cosmetic industries, cosmetic tools or articles for daily use, such as small brushes, are involved. Since the cosmetic tools or articles for daily use need to be used every day, and because their use types have particularity, they require to be washed and sterilized frequently. A typical method is performing a drying treatment by sunlight irradiation or using drying devices after washing, however, there is no specific sterilization device for a targeted treatment. Besides, they need to be stored in specific containers after washing and sterilization; at the same time, since cosmetic tools or specific living tools have different use types, they need to be stored separately. Thus, a plurality of containers for storage are needed, which leads to too many storage containers, and it is inconvenient to get the tools at any time in use.

SUMMARY OF THE INVENTION

It is one objective of the present application to provide a sterilization box, which aims at solving the problems that in the prior art, the cosmetic tools or the articles for daily use have no dedicated sterilization devices, and that the storage of the cosmetic tools or of the articles for daily use is inconvenient.

Technical solution is as follows: a sterilization box applicable to sterilize cosmetic tools comprises a base assembly, a housing assembly connected to the base assembly and cooperating with the base assembly to form a first cavity, and a supporting assembly connected in the first cavity and being able to connect with a plurality of cosmetic tools; the base assembly is provided therein with a second cavity; the sterilization box further comprises a circulation assembly configured to drive air circulations in the first cavity and in the second cavity and a sterilization assembly configured to sterilize the cosmetic tools; the circulation assembly comprises a first ventilation assembly cooperating with the second cavity and a second ventilation assembly cooperating with the first cavity; and a heating assembly cooperating with the first ventilation assembly is connected in the second cavity.

Further, the housing assembly comprises a first housing restrictedly connected to the base assembly and a second housing which is rotatable relative to the first housing and cooperates with the first housing to open or close.

Further, an upper end of the first housing is bent inwards to form a sliding slot in an arc shape, an upper end of the second housing is provided with an annular boss, and the annular boss is slidably connected in the sliding slot.

Further, the supporting assembly comprises a first sleeve member of which a lower end sleeve member is connected to the base assembly, and a second sleeve member of which an upper end sleeve member is connected to an inner wall of an upper end of the housing assembly; a third sleeve member is connected between the first sleeve member and the second sleeve member, and the third sleeve member is rotatably connected on the first sleeve member.

Further, the third sleeve member is provided thereon with multiple position limiting slots; the multiple position limiting slots are arranged circularly and at intervals; and each of the position limiting slots is restrictedly connected with a clamp member configured to clamp the cosmetic tools.

Further, the base assembly comprises a supporting base in an annular shape, a first cover connected to a bottom of the supporting base, and a second cover connected to a top of the supporting base; the lower end of the first sleeve member is connected to the second cover, the sterilization assembly is connected on the second cover, and the heating assembly is connected between the first cover and the second cover.

Further, the sterilization assembly comprises an ultraviolet lamp connected on the second cover, a lamp cover covering on the ultraviolet lamp, and a first printed circuit board (PCB) electrically connected with the ultraviolet lamp.

Further, an upper end face of the supporting base is connected with a third cover, the third cover is provided with a plurality of connecting supports, and the heating assembly comprises a plurality of heating bodies connected to the connecting supports and a second printed circuit board electrically connected with the heating bodies.

Further, the first ventilation assembly comprises a first ventilation fan connected on a bottom of the third cover, first ventilation holes defined on the first cover, second ventilation holes defined on the second cover, and a third ventilation hole defined on the third cover; and the third ventilation hole is located at a central part of the third cover and aligned with the first ventilation fan.

Further, the second ventilation assembly comprises a second ventilation fan connected to the upper end of the second sleeve member, at least one fourth ventilation hole defined on a wall of the second sleeve member, and a ventilation pipe connected to an upper part of the housing assembly.

Compared with the prior art, the sterilized box provided by the present application possesses the following technical effects: the first cavity being able to accommodate multiple cosmetic tools is enclosed by the housing assembly and the base assembly, the base assembly is provided therein with the second cavity, and at the same time the circulation assembly arranged on the base assembly heats and circulates the air in the first cavity and the second cavity via the heating assembly, the first ventilation assembly, and the second ventilation assembly, so as to dry the cosmetic tools after washing. Besides, the first ventilation assembly and the heating assembly cooperate with the second cavity, and the second ventilation assembly cooperates with the first cavity, so that the air entering via the first ventilation assembly is heated and then discharged out via the second ventilation assembly in the upper position, thereby ensuring the dryness of the air inside the first cavity. Meanwhile, the arrangement of the sterilization assembly can also continuously sterilize the cosmetic tools, thereby ensuring the cleanness of the cosmetic tools.

DETAILED DESCRIPTION OF THE EMBODIMENTS

Figure 1:
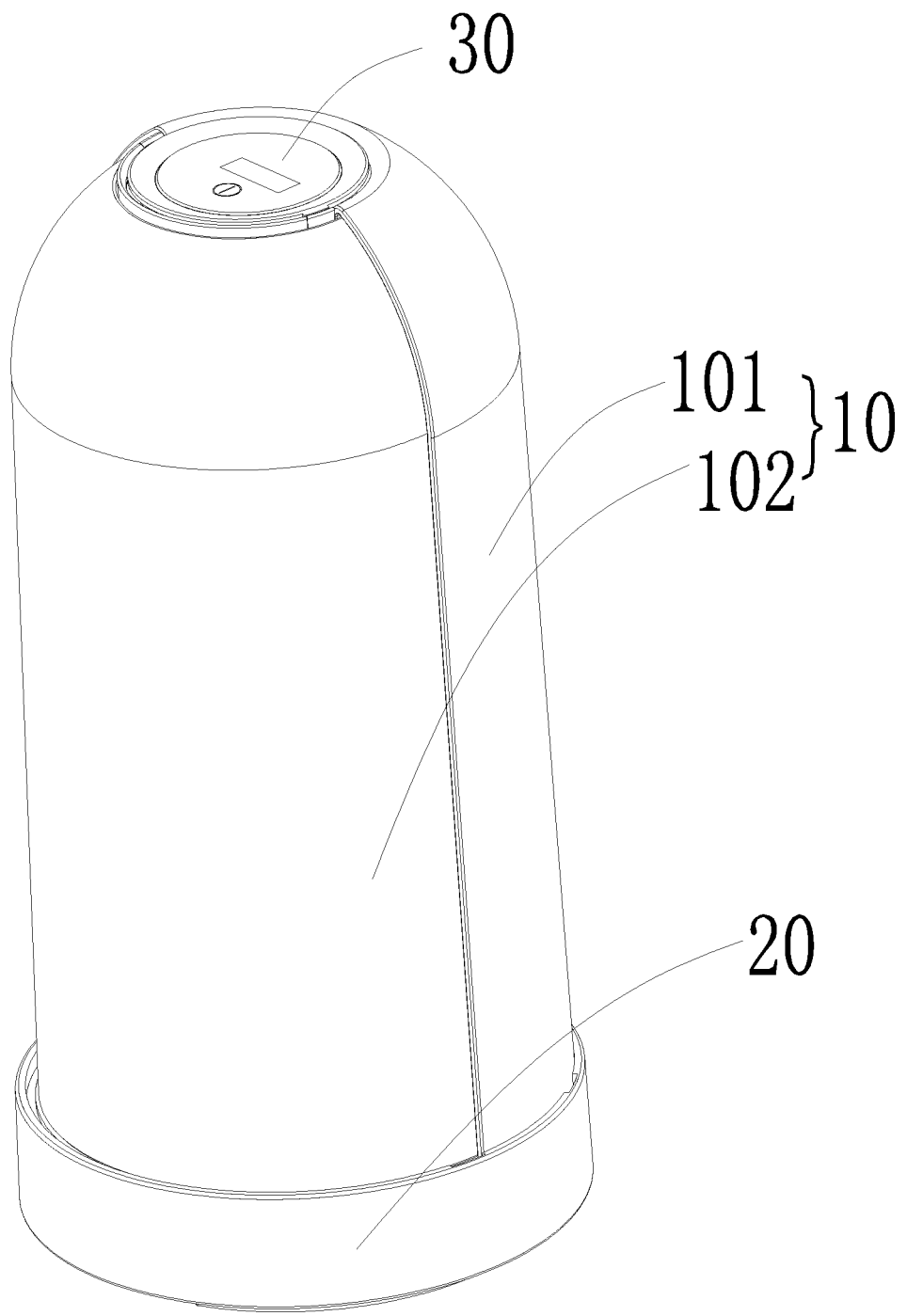
FIG. 1 is a perspective structural view of a sterilization box provided by one embodiment of the present application.
Figure 2:
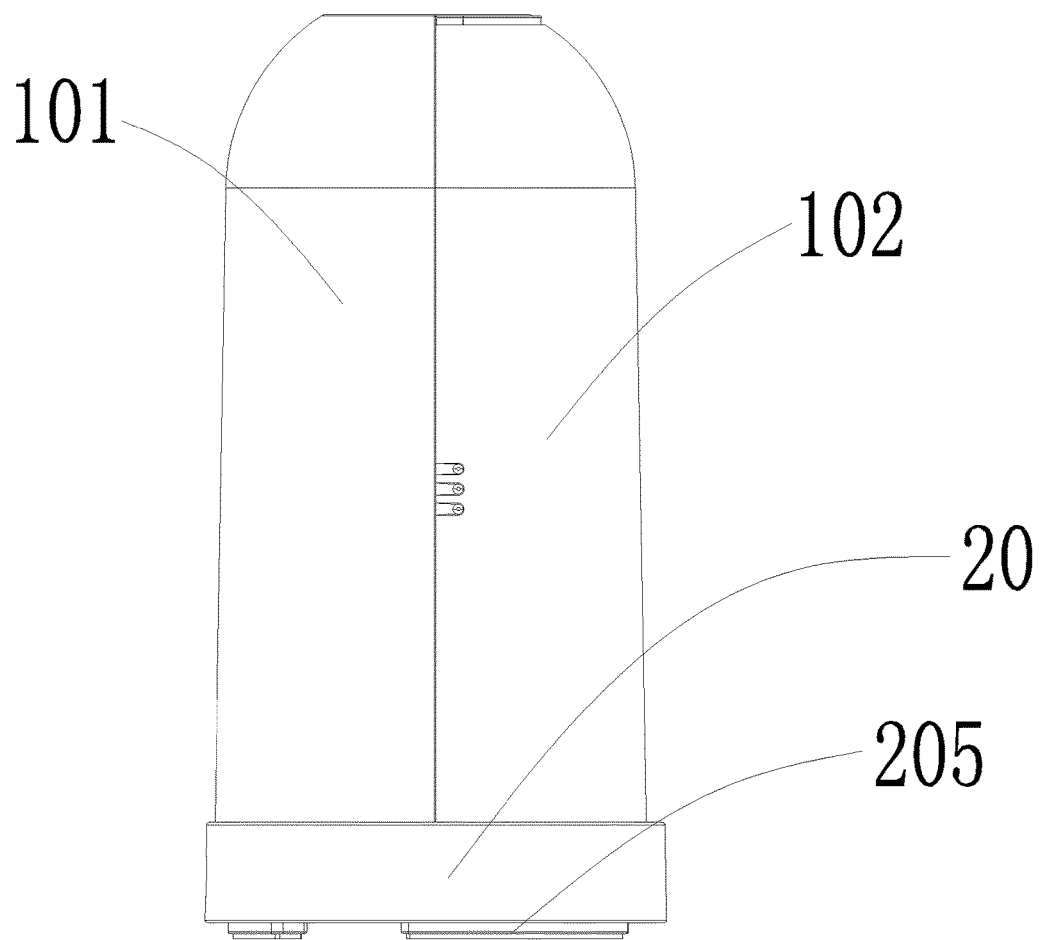
FIG. 2 is a left view of a sterilization box provided by one embodiment of the present application.

In order to make the purposes, technical solutions, and advantages of the present invention be clearer and more understandable, the present invention will be further described in detail hereinafter with reference to the accompanying drawings and embodiments. It should be understood that the embodiments described herein are only intended to illustrate but not to limit the present application.

It should be noted that when an element is described as "fixed" or "arranged" on/at another element, it means that the element can be directly or indirectly fixed or arranged on/at another element. When an element is described as "connected" to/with another element, it means that the element can be directly or indirectly connected to/with another element.

It also should be noted that the position terms in the embodiments of the present application, such as "left", "right", "on", "above", "beneath", etc., are merely mutually relative concepts or take a normal use state of a product as a reference, but should not be considered as any limitation.

Referring to FIGS. 1-5, in embodiments of the present application, a sterilization box, applicable to sterilize cosmetic tools, is provided. The cosmetic tools particularly refer to brush tools for coating cosmetic powder. The sterilization box comprises a base assembly 20, a housing assembly 10, connected to the base assembly 20 and cooperating with the base assembly 20 to form a first cavity 104, and a supporting assembly 40 connected in the first cavity 104 and being able to connect with a plurality of cosmetic tools. The housing assembly 10 is preferably an integral transparent structure. The base assembly 20 is provided therein with a second cavity 2011. The sterilization box further comprises a circulation assembly configured to drive air circulations in the first cavity 104 and the second cavity 2011, and a sterilization assembly 50 configured to sterilize the cosmetic tools. The circulation assembly comprises a first ventilation assembly 70 cooperating with the second cavity 2011 and a second ventilation assembly 80 cooperating with the first cavity 104. A heating assembly 60 cooperating with the first ventilation assembly is connected in the second cavity 2011. In this embodiment, air in the second cavity 2011 is heated by the heating assembly 60 and blown by the first ventilation assembly 70 into the first cavity 104 to dry the cosmetic tools. Air containing water vapor is discharged from inside of the first cavity 104 to outside of the first cavity 104 by the second ventilation assembly 80.

In the sterilization box of the above design, the housing assembly 10 cooperates with the base assembly 20 to form the first cavity 104 that is able to accommodate the multiple cosmetic tools. The base assembly 20 is provided therein with the second cavity 2011. The circulation assembly arranged on the base assembly 20 heats and circulates air in the first cavity 104 and the second cavity 2011 through the heating assembly 60, the first ventilation assembly 70, and the second ventilation assembly 80, so as to dry cosmetic tools after washing. Furthermore, the first ventilation assembly 70 and the heating assembly 60 are connected to the base assembly 20 at the lower position. The second ventilation assembly 80 is connected to an upper part of the supporting assembly 40, thus enabling the air entering from the first ventilation assembly 70 to be discharged via the second ventilation assembly 80 in the upper position after being heated, and further ensuring the dryness of the air inside the first cavity 104. Meanwhile, the arrangement of sterilization assembly 50 is able to continuously sterilize the cosmetic tools at the same time, thereby ensuring the cleanness of the cosmetic tools.

In one embodiment of the present application, as shown in FIGS. 1-5, the housing assembly 10 is preferably formed by connecting a cylinder housing and a bowl-shaped structure together. The bowl-shaped structure is invertedly arranged above the housing assembly. A lower part of the cylinder structure is connected to the base assembly 20. An end part of the bowl-shaped structure is further connected to a liquid crystal display (LCD) device 30 for displaying a work state and a work time. The LCD device 30 can be remotely controlled after being communicated with an application of a mobile phone.

Figure 4:
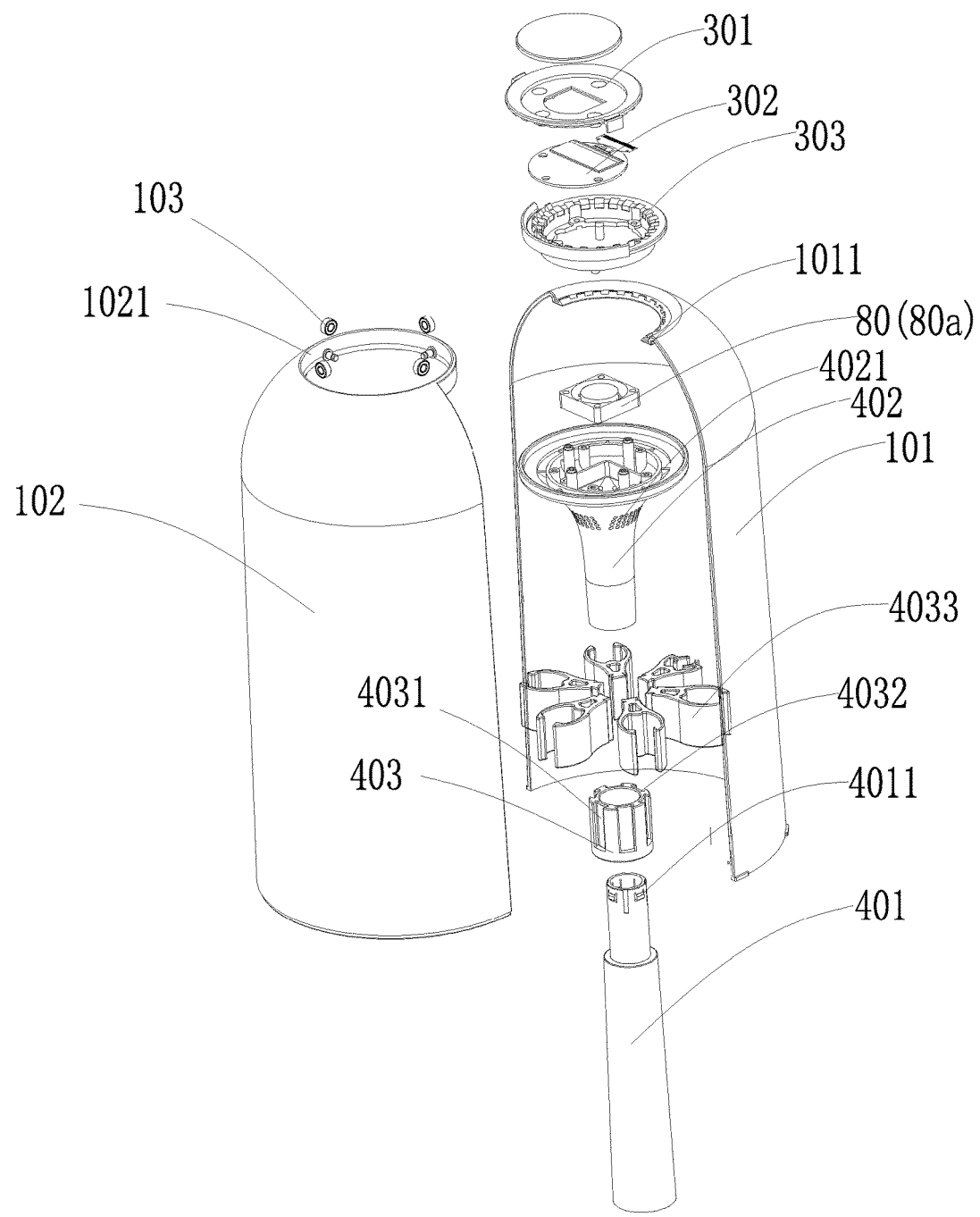
FIG. 4 is an exploded view of a housing assembly and inner structures thereof of a sterilization box provided by one embodiment of the present application.

Specifically, as shown in FIG. 4, in one embodiment of the present application, the housing assembly 10 comprises a first housing 101 restrictedly connected to the base assembly 20 and a second housing 102 that is rotatable relative to the first housing 10 and cooperates with the second housing 102 to open or close. The first housing 101 and the second housing 102 are respectively two halves of the structure of the housing assembly 10. The second housing 102 can be rotated to coincide with the first housing 101 and thereby realize the opening of the housing assembly 10, or rotated to a position opposite to the first housing 101 and thereby realize the closing of the housing assembly 10.

Specifically, as shown in FIG. 4, in one embodiment of the present application, an upper end of the first housing 101 is bent inwards to form an arc-shaped sliding slot 1011. An upper end of the second housing 102 is provided with an annular boss 1021. The annular boss 1021 is slidably connected in the sliding slot 1011. A plurality of bearing members 103 for assisting the sliding are arranged between the annular boss 1021 and the sliding slot 1011.

In this embodiment, as shown in FIG. 4, the second housing 102 is relatively located beneath the first housing 101. A top end of the first housing 101 is connected to a circular supporting cover 303 supporting the LCD device 30. The LCD device 30 comprises an LCD panel 301 restrictedly connected to a top end of the supporting cover 303, and a display controlling member 302 connected to a bottom of the supporting cover 303. The display controlling member 302 is electrically connected with the LCD panel 301.

Figure 3:
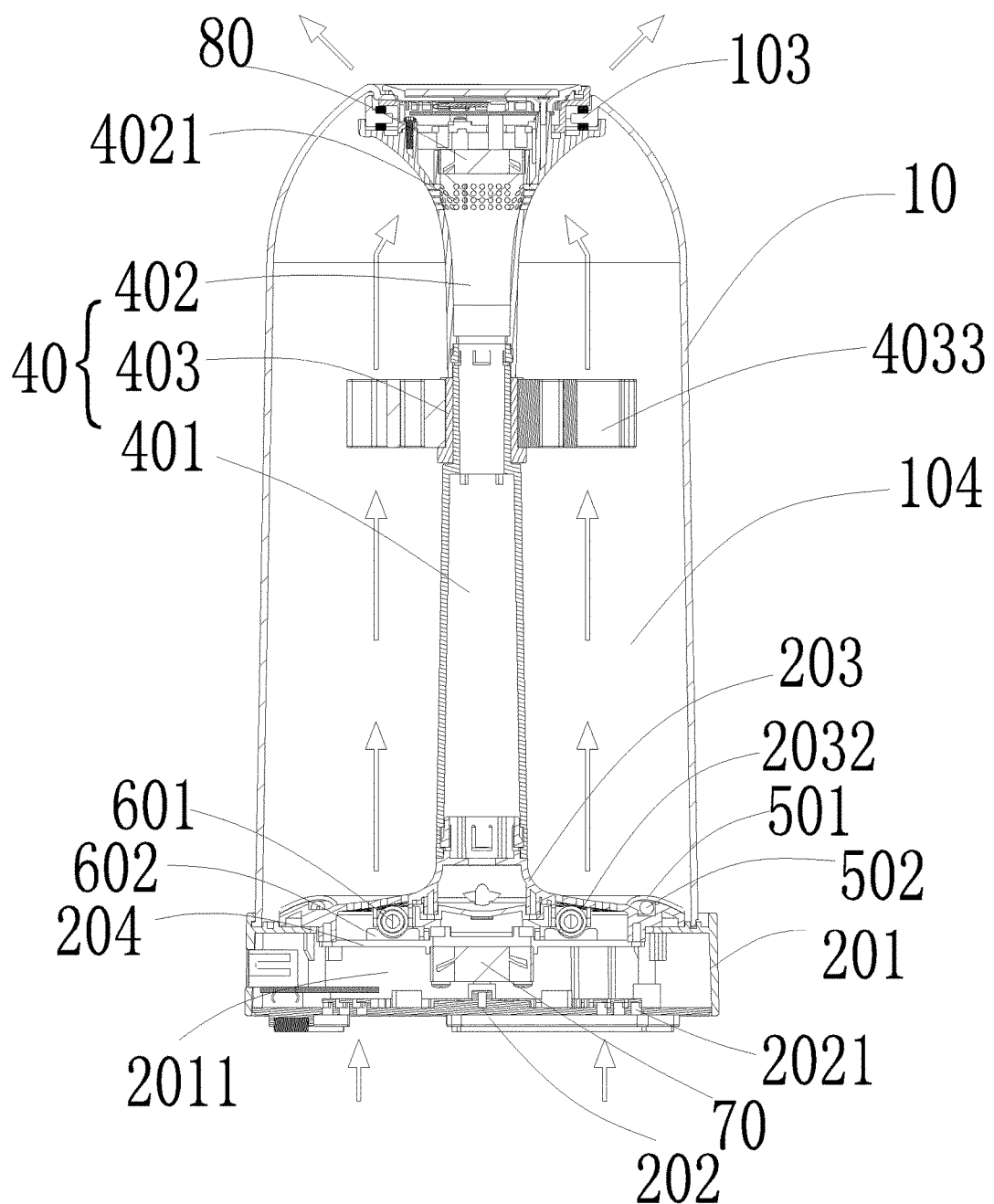
FIG. 3 is a partially cut-away view of a sterilization box provided by one embodiment of the present application.

Specifically, as shown in FIGS. 3-4, in one embodiment of the present application, the supporting assembly 40 comprises a first sleeve member 401 of which a lower end is connected to the base assembly 20, and a second sleeve member 402 of which an upper end is connected to an inner wall of an upper end of the housing assembly 10. A third sleeve member 403 is connected between the first sleeve member 401 and the second sleeve member 402, and the third sleeve member 403 is rotatably connected on the first sleeve member 401.

In this embodiment, a lower end of the second sleeve member 402 is restrictedly connected in an upper end of the first sleeve member 401, and then the third sleeve member 403 is restrictedly and rotatably connected to the first sleeve member 401.

In this embodiment, as shown in FIG. 4, an upper end of the third sleeve member 403 is provided with an annular shrink opening 4032. An inner diameter of the annular shrink opening 4032 is larger than or equal to an outer diameter of the second sleeve member 402, and is smaller than an outer diameter of the first sleeve member 401; moreover, an inner diameter of the lower end of the third sleeve member 403 is larger than an outer diameter of the first sleeve member 401. Such a design allows the third sleeve member 403 to be rotatably connected on the first sleeve member 401. In addition, an outer surface of the first sleeve member 401 is provided with outward first locking bosses 4011, and an inner wall of the third sleeve member 403 is concaved to form first locking slots (not shown in the figures) matching with the first locking bosses 4011. The first locking bosses 4011 are engaged in the first locking slots to make the third sleeve member 403 be restrictedly connected to the first sleeve member 401.

Specifically, as shown in FIG. 4, in one embodiment of the present application, an outer surface of the third sleeve member 403 is concaved to form multiple position limiting slots 4031. The position limiting slots 4031 are arranged circularly and at intervals. Each of the position limiting slots 4031 is restrictedly connected with a clamp member 4033 configured to clamp the cosmetic tools. Such a design enables the cosmetic tools to be connected to the third sleeve member 403 through the clamp members 4033, and meanwhile the user can rotate the cosmetic tools and get the desired one according to his/her need.

In this embodiment, the clamp members 4033 are horizontally arranged so that the cosmetic tools can be vertically connected to the clamp members 4033. Meanwhile, in order to meet different diameters of different cosmetic tools, the clamp members 4033 of different sizes can be pre-designed.

Figure 5:
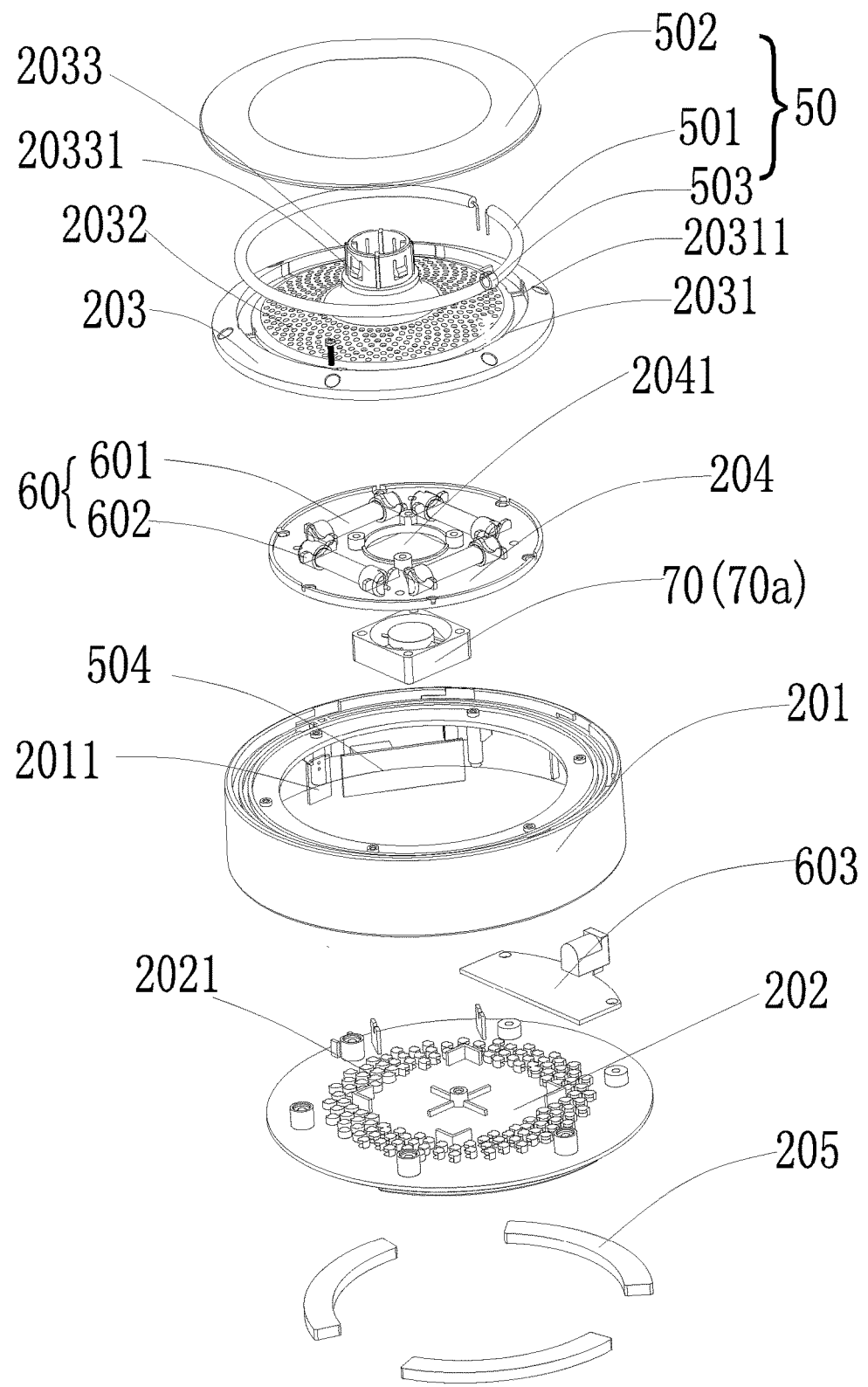
FIG. 5 is an exploded view of a base assembly and inner structures thereof of a sterilization box provided by one embodiment of the present application.

Specifically, as shown in FIGS. 3 and 5, in one embodiment of the present application, the base assembly 20 comprises a supporting base 201 in an annular shape, a first cover 202 connected to a bottom of the supporting base 201, and a second cover 203 connected to a top of the supporting base 201. A lower end of the first sleeve member 401 is connected to the second cover 203. The sterilization assembly 50 is connected on the second cover 203. The heating assembly 60 is connected between the first cover 202 and the second cover 203. The second cavity 2011 is enclosed by the supporting base 201, the first cover 202, and the second cover 203.

In this embodiment, as shown in FIGS. 3 and 5, both a lower end of the first housing 101 and a lower end of the second housing 102 are connected to an upper end face of the supporting base 201. The second cover 203 is located at a bottom of the first cavity 104. A top end of the second cover 203 is provided with a connecting member 2033 connected with the first sleeve member 401. An outer wall of the connecting member 2033 protrudes to form second locking bosses 20331, and an inner wall of a bottom end of the first sleeve member 401 is concaved to form second locking slots (not shown in the figures). The second locking bosses 20331 are locked inside the second locking slots to realize the connection between the first sleeve member 401 and the second cover 203.

In one embodiment of the present application, as shown in FIGS. 3 and 5, a bottom of the first cover 202 is connected to an anti-sliding pad 205 for preventing the sterilization box from sliding.

Specifically, as shown in FIGS. 3 and 5, in one embodiment of the present application, an upper surface of the second cover 203 is concaved to form an annular-shaped accommodating slot 2031. The sterilization assembly 50 comprises an ultraviolet lamp 501 connected in the accommodating slot 2031, a lamp cover 502 covering the ultraviolet lamp 501, and a first PCB 504 electrically connected with the ultraviolet lamp 501.

In this embodiment, as shown in FIGS. 3 and 5, the first PCB 504 is electrically connected with the second housing 102. The first PCB 504 is electrically connected with a toggle switch 2011 connected to the supporting base 201. When the second housing 102 is rotated to close the housing assembly, the second housing 102 triggers the toggle switch 2011, and the first PCB 504 controls the ultraviolet lamp 501 to sterilize the cosmetic tools in the first cavity 104. When the second housing 102 is rotated to open the housing assembly, the toggle switch 2011 is returned by the second housing 102, the first PCB 504 controls the ultraviolet lamp 501 to stop working. Such a design is able to effectively save the energy consumption of the sterilization box.

In this embodiment, as shown in FIG. 5, the accommodating slot 2031 is provided therein with multiple locking recesses 20311, and multiple locking members 503 for preventing the ultraviolet lamp 501 from moving are sheathed on a light tube of the ultraviolet lamp 501. The locking members 503 are restrictedly connected to the locking recess 20311.

Specifically, as shown in FIGS. 3 and 5, in one embodiment of the present application, an upper end face of the supporting base 201 is connected with a third cover 204. The third cover 204 is provided thereon with a plurality of connecting supports 602. The heating assembly comprises a plurality of heating bodies 601 connected on the connecting supports 602 and a second PCB 603 electrically connected with the heating bodies 601.

In this embodiment, as shown in FIGS. 3 and 5, a longitudinal section of the second cover 203 is in an arc shape bending upwards. The third cover 204 is accommodated between the second cover 203 and the supporting base 201. The heating bodies connected on the third cover 204 are sequentially connected in an end-to-end manner, and restrictedly connected on the connecting supports 602, which can facilitate centralized heating of the heating bodies 601.

Specifically, as shown in FIGS. 3 and 5, in one embodiment of the present application, the first ventilation assembly 70 comprises a first ventilation fan 70a connected to a bottom of the third cover 204, first ventilation holes 2021 defined in the first cover 202, second ventilation holes 2032 defined in the second cover 203, and a third ventilation hole 2041 defined in the third cover 204. The third ventilation hole 2041 is located at a central part of the third cover 204 and aligned with the first ventilation fan 70a.

In this embodiment, as shown in FIGS. 3 and 5, the multiple heating bodies 601 are connected in an end-to-end manner, and restrictedly connected on the connecting supports 602. The third ventilation hole 2041 is located at a center of a structure formed by the heating bodies 601. Besides, an air outlet of the first ventilation fan 70a is aligned with the third ventilation hole 2041, in this way, the air suctioned through the first ventilation fan 70a can be heated more quickly.

In this embodiment, water residue on the cosmetic tools after washing can drop on the third cover 204 via the second ventilation hole 2032, and then the heating bodies on the third cover 204 evaporate the water residue. Such a design avoids water accumulation in the sterilization box.

In this embodiment, as shown in FIGS. 3 and 5, the number of the first ventilation holes 2021 is a plural, and the first ventilation holes 2021 are all distributed on the first cover 202. Air outside the sterilization box is suctioned by the first ventilation fan 70a via the first ventilation holes 2021, introduced via the third ventilation holes 2041 to the heating bodies for heating, and then enters the first cavity 104 through the second ventilation holes 2032 in the second cover 203, such that it can perform a drying process for the cosmetic tools connected in the first cavity 104.

Specifically, as shown in FIGS. 3 and 5, in one embodiment of the present application, the second ventilation assembly 80 comprises a second ventilation fan 80a connected to an upper end of the second sleeve member 402, at least one fourth ventilation hole 4021 defined in a wall of the second sleeve member 402, and a ventilation pipe (not shown in the figures) connected to an upper part of the housing assembly 10.

In one embodiment of the present application, the second ventilation fan 80a is used to draw the air from the first cavity 104 via the fourth ventilation holes 4021 and then discharge the air out of the first cavity 104 via the ventilation pipe arranged on the upper part of the housing assembly 10.

The aforementioned embodiments are only preferred embodiments of the present application, and are not used for limiting the present invention. Any modification, equivalent replacement, improvement, and so on, which are made within the spirit and the principle of the present application, should be included in the protection scope of the present application.

The invention claimed is:

1. A sterilization box, applicable to sterilize cosmetic tools, wherein,
the sterilization box comprises a base assembly, a housing assembly connected to the base assembly and cooperating with the base assembly to form a first cavity, and a supporting assembly connected in the first cavity and being able to connect with a plurality of cosmetic tools; the base assembly is provided therein with a second cavity; the sterilization box further comprises a circulation assembly configured to drive air circulations in the first cavity and in the second cavity and a sterilization assembly configured to sterilize the cosmetic tools; the circulation assembly comprises a first ventilation assembly cooperating with the second cavity and a second ventilation assembly cooperating with the first cavity; and a heating assembly cooperating with the first ventilation assembly is connected in the second cavity; the supporting assembly comprises a first sleeve member of which a lower end is connected to the base assembly, and a second sleeve member of which an upper end is connected to an inner wall of an upper end of the housing assembly; a third sleeve member is connected between the first sleeve member and the second sleeve member, and the third sleeve member is rotatably connected on the first sleeve member;
the base assembly comprises a supporting base in an annular shape, a first cover connected to a bottom of the supporting base, and a second cover connected to a top of the supporting base; the lower end of the first sleeve member is connected to the second cover, the sterilization assembly is connected on the second cover, and the heating assembly is connected between the first cover and the second cover;
the sterilization assembly comprises an ultraviolet lamp connected on the second cover, a lamp cover covering on the ultraviolet lamp, and a first printed circuit board electrically connected with the ultraviolet lamp; and
an upper end face of the supporting base is connected with a third cover, the third cover is provided with a plurality of connecting supports, and the heating assembly comprises a plurality of heating bodies connected to the connecting supports and a second printed circuit board electrically connected with the heating bodies.

2. The sterilization box of claim 1, wherein, the first ventilation assembly comprises a first ventilation fan connected on a bottom of the third cover, first ventilation holes defined on the first cover, second ventilation holes defined on the second cover, and a third ventilation hole defined on the third cover; and the third ventilation hole is located at a central part of the third cover and aligned with the first ventilation fan.

3. The sterilization box of claim 2, wherein, the second ventilation assembly comprises a second ventilation fan connected to the upper end of the second sleeve member, at least one fourth ventilation hole defined on a wall of the second sleeve member, and a ventilation pipe connected to an upper part of the housing assembly.

4. The sterilization box of claim 1, wherein, the housing assembly comprises a first housing restrictedly connected to the base assembly and a second housing which is rotatable relative to the first housing and cooperates with the first housing to open or close.

5. The sterilization box of claim 1, wherein, an upper end of the first housing is bent inwards to form a sliding slot in an arc shape, an upper end of the second housing is provided with an annular boss, and the annular boss is slidably connected in the sliding slot.

6. The sterilization box of claim 1, wherein, the third sleeve member is provided thereon with multiple position limiting slots; the multiple position limiting slots are arranged circularly and at intervals; and each of the position limiting slots is restrictedly connected with a clamp member configured to clamp the cosmetic tools.

* * * * *